US006469034B1

(12) United States Patent
Uckun et al.

(10) Patent No.: US 6,469,034 B1
(45) Date of Patent: Oct. 22, 2002

(54) CYCLOHEXENYL-ETHYL-THIOUREA COMPOUNDS FOR INHIBITING HIV REVERSE TRANSCRIPTASE

(75) Inventors: Fatih M. Uckun, White Bear Lake, MN (US); Taracad K. Ventatachalam, St. Anthony, MN (US)

(73) Assignee: Parker Hughes Institute, St. Paul, MN (US)

( * ) Notice: Subject to any disclaimer, the term of this patent is extended or adjusted under 35 U.S.C. 154(b) by 0 days.

(21) Appl. No.: 09/338,686

(22) Filed: Jun. 23, 1999

(51) Int. Cl.[7] .......................... A61K 31/44; A61K 31/17

(52) U.S. Cl. ....................... 514/352; 514/349; 514/358; 514/580

(58) Field of Search .................................. 514/358, 277, 514/247, 255, 332, 352, 349, 580, 371

(56) References Cited

U.S. PATENT DOCUMENTS

| | | | |
|---|---|---|---|
| 5,593,993 A | 1/1997 | Morin, Jr. et al. | |
| 5,658,907 A | 8/1997 | Morin, Jr. et al. | |
| 5,686,428 A | 11/1997 | Eriksson et al. | |
| 5,714,503 A | 2/1998 | Morin, Jr. et al. | |

FOREIGN PATENT DOCUMENTS

| | | |
|---|---|---|
| EP | 0 540 143 A2 | 5/1993 |
| WO | WO 93/03022 | 2/1993 |

OTHER PUBLICATIONS

Mao, C. et al., "Rational Design of N–[2–(2,5–Dimethoxyphenylethyl)]–N'–[2–(5–Bromopyridyl)]–Thiourea(HI–236) As A Potent Non–Nucleoside Inhibitor of Drug–Resistant Human Immunodeficiency Virus", Bioorganic & Medicinal Chemistry Letters, vol. 9 pp. 1593–1598 (1999).

Uckun, F. et al. "N–[2–(1–Cyclohexenyl)Ethyl]–N'–[2–(5–Bromopyridyl)]–Thiourea and N'–[2–(1–Cyclohexenyl)Ethyl]–N'–[2–(5–Chloropyridyl)]–Thiourea As Potent Inhibitors of Multidrug–Resistant Human Immunodeficiency Virus–1", Bioorganic & Medicinal Chemistry Letters, vol. 9 pp. 2721–2726, (1999).

Ahgren, C., et al., 1995, Antimicrob. Agents Chemotherapy, 39, 1329–1335 The PETT Series, a New Class of Potent Nonnucleoside Inhibitors of Human Immunodeficiency Virus Type 1 Reverse Transcriptase.

Bell, F. W., et al., 1995, J. Med. Chem., 38, 4929–4936 Penethylthiazolethiourea (PETT) Compounds, a New Class of HIV–1 Reverse Transcriptase Inhibitors. 1. Synthesis and Basic Structure—Activity Relationship Studies of PETT Analogs.

Bosworth, N., et al., 1989 Nature 341:167–168 Scintillation proximity assay.

Cantrell, A. S., et al., 1996, J. Med. Chem., 39, 4261–4274 Phenethylthiazolylthiourea (PETT) Compounds as a New Class of HIV–1 Reverse Transcriptase Inhibitors. 2. Synthesis and Further Structure—Activity Relationship Studies of PETT Analogs.

Das, K. et al., 1996, J. Mol. Biol., 264, 1085–1100 Crystal Structures of 8–C1 and 9–C1 TIBO Complexed with Wild-type HIV–1 RT and 8–C1 TIBO Complexed with the Tyr181Cys HIV–1 RT Drug–resistant Mutant.

Ding, J., 1995, et al., Nat. Struct. Biol., 2, 407–415 Structure of HIV–1 RT/TIBO R 86183 complex reveals similarity in the binding of diverse nonnucleoside inhibitors.

Erice, A. et al., 1993, Antimicrob. Ag. Chemother., 37, 835 Anti–Human Immunodeficiency Virus Type 1 Activity of an Anti–CD4 Immunoconjugate Containing Pokeweed Antiviral Protein.

Kohlstaedt, L.A. et al., 1992, Science, 256, 1783–1790 Crystal Structure at 3.5 Å Resolution of HIV–1 Reverse Transcriptase Complexed with an Inhibitor.

Mao, C. et al., 1998, Bioorganic & Medicinal Chemistry Letters 8, pp. 2213–2218 Structure–Based Design of N–[2–(1–Piperidinylethyl)]–N'–[2–(5–Bromopyridyl)] Thiourea and N–2–(1–Piperazinylethyl)–N'–[2–(5–Bromopyridyl)]–Thiourea as Potent Non–Nucleoside Inhibitors of HIV–1 Reverse Transcriptase.

Pauwels, R. et al., 1990, Nature, 343, 470–474 Potent and selective inhibitionof HIV–1 replication in vitro by a novel series of TIBO derivatives.

Ren, J. et al., 1995, Structure, 3, 915–926 The structure of HIV–1 reverse transcriptase complexed with 9–chloro–TIBO: lessons for inhibitor design.

Romero, D. L. et al., 1993, J. Med. Chem., 36, 1505–1508 Bis(heteroaryl)piperazine(BHAP)Reverse Transcriptase Inhibitors: Structure–Activity Relationships of Novel Substituted Indole Analogues and the Identification of 1–[(5–Methanesulfonamido–1H–indol–2–yl)–carbonyl]–4–[3–[(1–methylethyl)amino]–pyridinyl]piperazine Monomethanesulfonate(U–90152S), a Second–Generation Clinical Candidate.

Sahlberg, et al., 1998, Bioorganic & Medicinal Chemistry Letters 8, pp. 1511–1516 Synthesis and Anti–Hiv Activities of Urea–PETT Analogs Belonging to a New Class of Potent Non–Nucleoside HIV–1 Reverse Transcriptase Inhibitors.

(List continued on next page.)

Primary Examiner—Russell Travers
Assistant Examiner—S. Jiang
(74) Attorney, Agent, or Firm—Merchant & Gould P.C.

(57) ABSTRACT

Novel CycloHexenyl-Ethyl-Thiourea (CHET) compounds as inhibitors of reverse transcriptase and effective agents for the treatment of HIV infection, including mutant, drug-sensitive, drug-resistant, and multi-drug resistant strains of HIV.

2 Claims, No Drawings

OTHER PUBLICATIONS

Sudbeck, E. A. et al., 1998, *Antimicrobial Agents and Chemotherapy*, 42(12), 3225–33 Structure–Based Design of Novel Dihydroalkoxybenzyloxopyrimidine Derivatives as Potent Nonnucleoside Inhibitors of the Human Immunodeficiency Virus Reverse Transcriptase.

Uckun, F. M. et al., 1998, *Antimicrobial Agents and Chemotherapy, 42*, 383 TXU (Anti–CD7)–Pokeweed Antiviral Protein as a Potent Inhibitor of Human Immunodeficiency Virus.

Vig, R. et al., 1998, *Bioorganic & Medicinal Chemistry*, 6:1789–1797 Rational Design and Synthesis of Phenethyl–5–bromopyridyl Thiourea Derivatives as Potent Non–nucleoside Inhibitors of HIV Reverse Transcriptase.

Zhang et al., 1996, *Antiviral Chemistry & Chemotherapy*, 7(5):221–229 Synergistic inhibition of HIV–1 reverse transcriptase and HIV–1 replication by combining trovirdine with AZT, ddl and ddc in vitro.

CYCLOHEXENYL-ETHYL-THIOUREA COMPOUNDS FOR INHIBITING HIV REVERSE TRANSCRIPTASE

FIELD OF THE INVENTION

The invention relates to inhibitors of reverse transcriptase effective against HIV, including mutant strains of HIV, and effective in the treatment of multi-drug resistant HIV infection.

BACKGROUND OF THE INVENTION

Agents currently used to treat HIV infection attempt to block replication of the HIV virus by blocking HIV reverse transcriptase or by blocking HIV protease. Three categories of anti-retroviral agents in clinical use are nucleoside analogs (such as AZT), protease inhibitors (such as nelfinavir), and the recently introduced non-nucleoside reverse transcriptase inhibitors (NNI), such as nevirapine.

The recent development of potent combination anti-retroviral regimens has significantly improved prognosis for persons with HIV and AIDS. Combination therapies may be a significant factor in the dramatic decrease in deaths from AIDS (a decrease in death rate as well as absolute number). The most commonly used combinations include two nucleoside analogs with or without a protease inhibitor.

Nevirapine is currently the only NNI compound which has been used in combination with AZT and/or protease inhibitors for the treatment of HIV. A new series of effective drug cocktails will most likely involve other NNIs in combination with nucleoside and protease inhibitors as a triple action treatment to combat the growing problem of drug resistance encountered in single drug treatment strategies.

The high replication rate of the virus unfortunately leads to genetic variants (mutants), especially when selective pressure is introduced in the form of drug treatment. These mutants are resistant to the anti-viral agents previously administered to the patient. Switching agents or using combination therapies may decrease or delay resistance, but because viral replication is not completely suppressed in single drug treatment or even with a two drug combination, drug-resistant viral strains ultimately emerge. Triple drug combinations employing one (or two) nucleoside analogs and two (or one) NNI targeting RT provide a very promising therapy to overcome the drug resistance problem. RT mutant strains resistant to such a triple action drug combination would most likely not be able to function.

Dozens of mutant strains have been characterized as resistant to NNI compounds, including L1001, K103N, V106A, E138K, Y181C and Y188H. In particular, the Y181C and K103N mutants may be the most difficult to treat, because they are resistant to most of the NNI compounds that have been examined.

Recently, a proposed strategy using a knock-out concentration of NNI demonstrated very promising results. The key idea in this strategy is to administer a high concentration of NNI in the very beginning stages of treatment to reduce the virus to undetectable levels in order to prevent the emergence of drug-resistant strains. The ideal NNI compound for optimal use in this strategy and in a triple action combination must meet three criteria:

1) very low cytotoxicity so it can be applied in high doses;
2) very high potency so it can completely shut down viral replication machinery before the virus has time to develop resistant mutant strains; and
3) robust anti-viral activity against current clinically observed drug resistant mutant strains.

Novel NNI designs able to reduce RT inhibition to sub-nanomolar concentrations with improved robustness against the most commonly observed mutants and preferably able to inhibit the most troublesome mutants are urgently needed. New antiviral drugs will ideally have the following desired characteristics: (1) potent inhibition of RT; (2) minimum cytotoxicity; and (3) improved ability to inhibit known, drug-resistant strains of HIV. Currently, few anti-HIV agents possess all of these desired properties.

Two non-nucleoside inhibitors (NNI) of HIV RT that have been approved by the U.S. Food and Drug Administration for licensing and sale in the United States are nevirapine (dipyridodiazepinone derivative) and delavirdine (bis(heteroaryl)piperazine (BHAP) derivative, BHAP U-90152). Other promising new non-nucleoside inhibitors (NNIs) that have been developed to inhibit HIV RT include dihydroalkoxybenzyloxopyrimidine (DABO) derivatives, 1-[(2-hydroxyethoxy)methyl]-6-(phenylthio)thymine (HEPT) derivatives, CHETrahydrobenzondiazepine (TIBO), 2',5'-Bis-O-(tert-butyldimethylsilyl)-3'-spiro-5"-(4"-amino-1",2"-oxathiole-2",2'-dioxide)pyrimidine (TSAO), oxathiin carboxanilide derivatives, quinoxaline derivatives, thiadiazole derivatives, and phenethylthiazolylthiourea (PETT) derivatives.

NNIs have been found to bind to a specific allosteric site of HIV-RT near the polymerase site and interfere with reverse transcription by altering either the conformation or mobility of RT, thereby leading to a noncompetitive inhibition of the enzyme (Kohlstaedt, L. A. et al., *Science*, 1992, 256, 1783–1790).

A number of crystal structures of RT complexed with NNIs have been reported (including α-APA, TIBO, Nevirapine, and HEPT derivatives), and such structural information provides the basis for further derivatization of NNI aimed at maximizing binding affinity to RT. However, the number of available crystal structures of RT NNI complexes is limited.

Given the lack of structural information, alternate design procedures must be relied upon for preparing active inhibitors such as PETT and DABO derivatives. One of the first reported strategies for systematic synthesis of PETT derivatives was the analysis of structure-activity relationships independent of the structural properties of RT and led to the development of some PETT derivatives with significant anti-HIV activity (Bell, F. W. et al., *J. Med. Chem.*, 1995, 38, 4929–4936; Cantrell, A. S. et al., *J. Med. Chem.*, 1996, 39, 4261–4274).

A series of selected phenethylthiazolylthiourea (PETT) derivatives targeting the NNI binding site of HIV reverse transcriptase (RT) were synthesized and tested for anti-human immunodeficiency virus (HIV) activity. The structure based design and synthesis of these PETT derivatives were aided by biological assays and their anti-HIV activity. Some of these novel derivatives were more active than AZT or Troviridine and abrogated HIV replication at nanomolar concentrations without any evidence of cytotoxicity. These compounds are useful in the treatment of HIV infection, and have particular efficacy against mutant strains, making them useful in the treatment of multi-drug resistant HIV.

SUMMARY OF THE INVENTION

The invention provides cyclohexenyl-ethyl-thiourea (CHET) compounds as newly identified non-nucleoside inhibitors (NNI) of HIV reverse transcriptase. The CHET compounds, compositions, and methods of the invention are useful in the treatment of HIV infection, with particular efficacy against multiple strains of HIV, including multi-drug resistant mutant strains.

The CHET compounds, compositions, and methods of the invention are useful for inhibiting reverse transcriptase activity and inhibiting replication of multiple strains of HIV, including therapy-naive, drug-resistant, and multi-drug resistant strains. In particular, the CHET compounds of the invention are useful for treating retroviral infection in a subject, such as an HIV-1 infection, by administration of the CHET compounds of the invention, for example, in a pharmaceutical composition.

The CHET compounds of the invention contain a cyclohexne structure as shown in Formula I. The cyclohexene may be substituted or unsubstituted ($R_n$). $R_1$ is a cyclic moiety which may be substituted or unsubstituted (X). The cyclic moiety can be aromatic and/or heterocyclic. X can be H, halo, nitro, or $CF_3$. X is preferably halo, and most preferably is Br or Cl. In a preferred embodiment, $R_1$ is pyridinyl, preferably substituted (X) with Br or Cl. Exemplary CHET compounds of the invention are HI-346 and HI 445, having the specific structure shown in Formula II, where X is Br (HI-346) or Cl (HI-445).

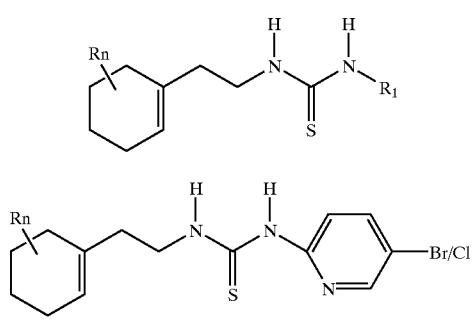

The CHET compounds and compositions useful in the invention exhibit:

1. very low cytotoxicity;
2. very high potency; and
3. potent activity against at least one clinically observed drug resistant mutant strain.

Specific compounds and methods of the invention are described more fully in the Detailed Description and in the Examples below.

DETAILED DESCRIPTION OF THE INVENTION

Definitions

When used herein, the following terms have the indicated meanings:

"NNI" means non-nucleoside inhibitor. In the context of the invention, non-nucleoside inhibitors of HIV reverse transcriptase (RT) are defined.

"Mutant HIV" means a strain of HIV having one or more mutated or altered amino acids as compared with wild type.

"Multi-Drug Resistant HIV" means one or more HIV strain which is resistant to treatment with one or more chemotherapeutic agent.

"Therapeutically effective amount" is a dose which provides some therapeutic benefit on administration, including, in the context of the invention, reduced viral activity or viral load in a patient, and also including inhibition of viral RT activity and/or replication of virus.

Compounds of the Present Invention

Compounds of the present invention are cyclohexenyl-ethyl-thiourea (CHET) compounds useful as non-nucleoside inhibitors of RT having the formula I:

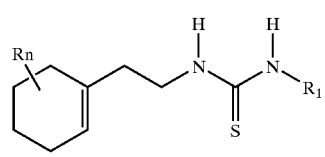

The cyclohexenyl may be substituted or unsubstituted ($R_n$), for example, R can be H, halogen, ($C_1$–$C_{12}$) alkyl or alkoxy, amino, cyano, nitro, hydroxy, and the like. The value of n can be 0 to 6.

$R_1$ is a cyclic moiety, which may be substituted or not (X), such as phenyl, pyridyl, pioeridinyl, piperonyl, morphoryl, furyl, and the like, and can be, for example, cyclo($C_3$–$C_{12}$) alkyl, cyclo($C_3$–$C_{12}$) alkenyl, isothiazolyl, tetrazolyl, triazolyl, pyridyl, imidazolyl, phenyl, napthyl, benzoxazolyl, benzimidazolyl, thiazolyl, oxazolyl, benzothiazolyl, pyrazinyl, pyridazinyl, thiadiazolyl, benzotriazolyl, pyrolyl, indolyl, benzothienyl, thienyl, benzofuryl, quinolyl, isoquinolyl, pyrazolyl, and the like.

In one preferred embodiment, $R_1$ is pyridyl, optionally substituted (X) with one or more substituents, for example, with an alkyl, alkoxy, halo, or hydroxy group. More preferably, $R_1$ is pyridyl substituted with a halogen such as bromine or chlorine. Exemplary compound of the invention are N-[2-(1-cyclohexenyl)ethyl-N-[2-(5-bromopyridyl)]-thiourea (HI-346) and N-[2-(1-cyclohexenyl)ethyl-N-[2-(5-chloropyridyl)]-thiourea (HI-445).

The compounds of the invention preferably bind to a specific allosteric site of HIV-RT near the polymerase site and interfere with reverse transcription, for example, by altering either the conformation or mobility of RT.

Acid Salts

The compounds of the invention may also be in the form of pharmaceutically acceptable acid addition salts. Pharmaceutically acceptable acid addition salts are formed with organic and inorganic acids. As used herein, the compounds of the invention include acid salts thereof.

Examples of suitable acids for salt formation are hydrochloric, sulfiuric, phosphoric, acetic, citric, oxalic, malonic, salicylic, malic, gluconic, fumaric, succinic, asorbic, maleic, methanesulfonic, and the like. The salts are prepared by contacting the free base form with a sufficient amount of the desired acid to produce either a mono or di, etc. salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R is hydrogen gives the corresponding basic salt.

Methods of Using the Compounds of the Invention

The compounds of the invention are useful in methods for inhibiting reverse transcriptase activity of a retrovirus. Retroviral reverse transcriptase is inhibited by contacting RT in vitro or in vivo, with an effective inhibitory amount of a compound of the invention. The compounds of the invention also inhibit replication of retrovirus, particularly of HIV, such as HIV-1. Viral replication is inhibited, for example, by contacting the virus with an effective inhibitory amount of a compound of the invention.

The methods of the invention are useful for inhibiting reverse transcriptase and/or replication of multiple strains of HIV, including mutant strains, and include treating a retroviral infection in a subject, such as an HIV-1 infection, by administering an effective inhibitory amount of a compound or a pharmaceutically acceptable acid addition salt of a compound of the Formula I. The compound or inhibitor of Formula I is preferably administered in combination with a pharmaceutically acceptable carrier, and may be combined with specific delivery agents, including targeting antibodies and/or cytokines. The compound or inhibitor of the invention may be administered in combination with other antiviral agents, immunomodulators, antibiotics or vaccines.

The compounds of Formula I can be administered orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories. In one embodiment, the CHET compounds of the invention can be applied intravaginally and/or topically, for example in gel form, for prevention of heterosexual transmission of HIV.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Dosage levels of approximately 0.02 to approximately 10.0 grams of a compound of the invention per day are useful in the treatment or prevention of retroviral infection, such as HIV infection, AIDS or AIDS-related complex (ARC), with oral doses 2 to 5 times higher. For example, HIV infection can be treated by administration of from about 0.1 to about 100 milligrams of compound per kilogram of body weight from one to four times per day. In one embodiment, dosages of about 100 to about 400 milligrams of compound are administered orally every six hours to a subject. The specific dosage level and frequency for any particular subject will be varied and will depend upon a variety of factors, including the activity of the specific compound the metabolic stability and length of action of that compound, the age, body weight, general health, sex, and diet of the subject, mode of administration, rate of excretion, drug combination, and severity of the particular ondition.

The compound of Formula I can be administered in combination with other agents seful in the treatment of HIV infection, AIDS or ARC. For example, the compound of the invention can be administered in combination with effective amounts of an antiviral, immunomodulator, anti-infective, or vaccine. The compound of the invention can be administered prior to, during, or after a period of actual or potential exposure to retrovirus, such as HIV.

Conjugation to a Targeting Moiety

The compound of the invention can be targeted for specific delivery to the cells to be treated by conjugation of the compounds to a targeting moiety. Targeting moiety useful for conjugation to the compounds of the invention include antibodies, cytokines, and receptor ligands expressed on the cells to be treated.

The term "conjugate" means a complex formed with two or more compounds.

The phrase "targeting moiety" means a compound which serves to deliver the compound of the invention to a specific site for the desired activity. Targeting moieties include, for example, molecules which specifically bind molecules present on a cell surface. Such targeting moieties useful in the invention include anti-cell surface antigen antibodies. Cytokines, including interleukins, factors such as epidermal growth factor (EGF), and the like, are also specific targeting moieties known to bind cells expressing high levels of their receptors.

Particularly useful targeting moieties for targeting the compounds of the invention to cells for therapeutic activity include those ligands that bind antigens or receptors present on virus-infected cells to be treated. For example, antigens present on T-cells, such as CD48, can be targeted with antibodies. Antibody fragments, including single chain fragments, can also be used. Other such ligand-receptor binding pairs are known in the scientific literature for targeting anti-viral treatments to target cells. Methods for producing conjugates of the compounds of the invention and the targeting moieties are known.

Methods of Making the Compounds of the Invention

The compounds of the invention may be prepared as shown in Schemes 1 and 2. In general, an appropriate pheneytylamine or pyridylethylamine ($R_1$—$NH_2$) is reacted with 1,1'-thiocarbonyl-diimidazole in acetonitrile solvent at ambient temperature for approximately 12 hours to form a thiocarbonyl reagent. The reaction product is then condensed with a substituted or non-substituted cyclohexenyl amine in an aprotic solvent such as dimethyl-formamide (DMF) at elevated temperature, such a 100° C., for an extended period of time such as about 15 hours. The desired CHET compound is purified by column chromatography.

Scheme 1

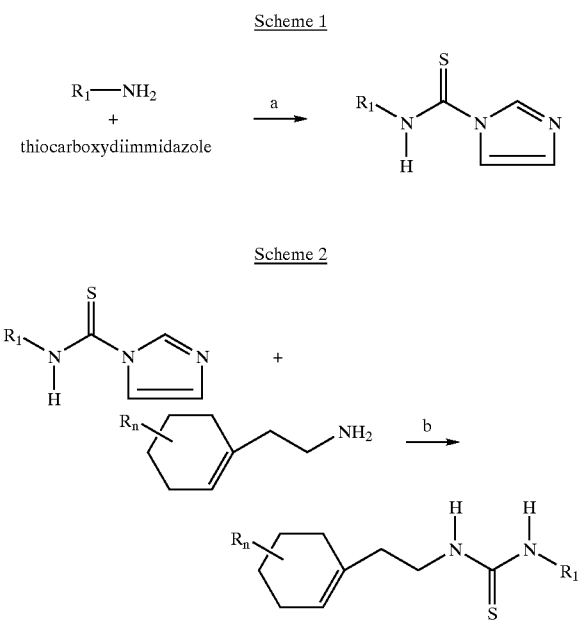

Scheme 2

The CHET compounds of the invention can be synthesized as described above, or by other, known synthetic methods.

EXAMPLES

The invention may be further clarified by reference to the following Examples, which serve to exemplify the embodiments, and not to limit the invention in any way.

Example 1

Synthesis and Characterization of Thiourea Inhibitors

In the present study, we replaced the pyridyl ring of trovirdine with a cyclohexenyl group that fits well with the Wing 2 region of the NNI binding pocket. The CHET compounds were synthesized as described in Scheme 1, in which a thiocarbonyl reagent was prepared from phenethylamine or pyridylethylamine and 1,1'-thiocarbonyldiimidazole in acetonitrile solvent at room temperature for 12 hours, and condensed with the appropriate 2-amino compounds in dimethyl fonmamide (DMF) at 100° C. for 15 hours. After work up, the derivatives were purified by column chromatography. Trovirdine was synthesized according to the literature procedure.

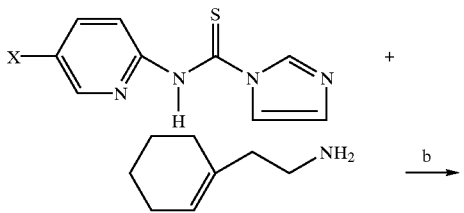

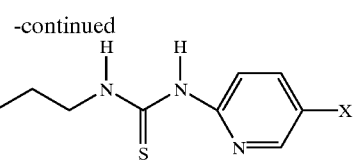

Characterization of Synthesized Compounds:

Proton and carbon nuclear magnetic resonance spectra were recorded on a Varian spectrometer using an automatic broad band probe. Unless otherwise noted, all NMR spectra were recorded in $CDCl_3$ at room temperature. The chemical shifts reported are in parts per million relative to tetramethyl silane as standard. The multiplicity of the signals were designated as follows: s, d, dd, t, q, m which corresponds to singlet, doublet, doublet of doublet, triplet, quartetand multiplet respectively. UV spectra were recorded from a Beckmann Model #DU 7400 UV/is spectrometer using a cell path length of 1 cm. Fourier Transform Infra Red spectra were recorded using an FT-Nicolet model Protege #460 instrument. The infra red spectra of the liquid samples were run as neat liquids using KBr discs. Mass spectrum analysis was conducted using either a Finnigan MAT 95 instrument or a Hewlett-Packard Matrix Assisted Laser Desorption (MALDI) spectrometer model #G2025A. The matrix used in the latter case was cyano hydoxy cinnamic acid. Melting points were determined using a Melt John's apparatus and uncorrected. Elemental analysis were was performed by Atlantic Microlabs (Norcross, Ga.). Column chromatography was performed using silica gel obtained from the Baker Company. The solvents used for elution varied depending on the compound and included one of the following : ethyl acetate, methanol, chloroform, hexane, methylene chloride and ether. Characterizataion data for the synthesized compounds is shown below:

N-[2-(5-Trifluoromethylpyridinyl)]-N'-[2-(1-Cyclohexenyl)ethyl]thiourea (HI-347) yield 40%; mp: 161–162° C.; UV(MeOH) $\lambda_{max}$: 208, 256, 276, 297 nm; IR(KBr) ν 3224, 3178, 3039, 2941, 2875, 2831, 1618, 1598, 1552, 1531, 1500, 1434, 1324, 1251, 1188, 1164, 1132, 1078, 1016, 933, 871, 827, 767, 719, 601 $cm^{-1}$; $^1$HNMR ($CDCl_3$) δ 11.38 (bs, 1H), 9.38 (bs, 1H), 8.39 (s, 1H), 7.86–7.82 (dd, 1H), 7.01–6.98 (d, 1H), 5.62 (s, 1H), 3.86–3.80 (q, 2H), 2.37–2.33 (t, 2H), 2.05–2.01 (m, 4H), 1.68–1.56 (m, 4H); $^{13}$C NMR ($CDCl_3$) δ 178.8, 155.2, 143.5, 135.6, 134.4, 124.1, 111.9, 44.3, 36.8, 27.7, 25.4, 22.8, 22.4;

N-[2-(5-Bromopyridinyl)]-N'-[2-(1-Cyclohexenyl)ethyl]thiourea (HI-346) yield 45%; mp: 172–173° C.; UV(MeOH) $\lambda_{max}$: 208, 275, 306 nm; IR(KBr) ν 3214, 3156, 3085, 3039, 2925, 2831, 1594, 1560, 1531, 1473, 1309, 1267, 1226, 1180, 1135, 1078, 1002, 918, 862, 821, 700, 505 $cm^{-1}$; $^1$H NMR ($CDCl_3$) δ 11.21 (bs, 1H), 9.42 (bs, 1H), 8.16–8.15 (d, 1H), 7.73–7.69 (dd, 1H), 6.88–6.85 (d, 1H), 5.59 (s, 1H), 3.84–3.78 (q, 2H), 2.35–2.31 (t, 2H), 2.05–1.99 (m, 4H), 1.67–1.55 (m, 4H); $^{13}$C NMR ($CDCl_3$) δ 178.6, 151.8, 146.3, 141.1, 134.5, 124.0, 113.6, 112.7, 44.1, 36.8, 27.7, 25.4, 22.8, 22.4;

N-[2-(5-Bromopyridinyl)]-N'-[2-(2-Adamantyl)]thiourea (HI-504) yield 49%; mp: 239–240° C.; WV(MeOH) $\lambda_{max}$: 206, 274, 306 nm; IR(KBr) ν 3207, 3151, 3081, 3031, 2906, 2844, 1591, 1556, 1531, 1469, 1332, 1309, 1270, 1226, 1193, 1172, 1135, 997, 862, 819, 723, 649 $cm^{-1}$; $^1$HNMR ($CDCl_3$) δ 11.51 (bs, 1H), 9.52 (bs, 1H), 8.25–8.24 (d, 1H), 7.74–7.71 (dt, 1H), 6.92–6.89 (d, 1H), 3.48–3.46 (d, 2H), 2.05–2.02 (bs, 3H), 1.78–1.63 (m, 12H); $^{13}$C NMR ($CDCl_3$) δ 179.1, 152.0, 146.3, 141.2, 113.7, 112.6, 57.9, 40.5, 36.9, 33.7, 28.2;

N-[2-(5-Bromopyridinyl)]-N'-[2-(2-Myrtanyl)]thiourea (HI-444) yield 55%; mp: 180–181° C.; UV(MeOH) $\lambda_{max}$: 208, 256, 275, 304 nm; IR(KBr) ν 3160, 3029, 2973, 2902, 2854, 1592, 1560, 1531, 1461, 1365, 1311, 1267, 1228, 1191, 1139, 1091, 1006, 825, 734, 692, 667, 509 cm$^{-1}$; $^1$HNMR(CDCl$_3$) δ 11.35 (bs, 1H), 9.74 (bs, 1H), 8.16 (s, 1H), 7.65–7.61 (dd, 1H), 6.90–6.87 (d, 1H), 3.70–3.65 (m, 2H), 2.41–2.28 (m, 2H), 1.95–85 (m, 5H), 1.56–1.51 (m, 1H), 1.14 (s, 3H), 1.04 (s, 3H), 0.89–0.86 (d, 1H); $^{13}$C NMR(CDCl$_3$) δ 178.7, 152.0, 146.2, 141.0, 113.8, 112.5, 51.2, 43.9, 41.2, 40.5, 38.6, 33.2, 27.9, 25.9, 23.2, 19.8;

N-[2-(5-Chloropyridinyl)]-N'-[2-(1-Cyclohexenyl)ethyl] thiourea (HI-445) yield 51%; mp: 165° C.; UV(MeOH) $\lambda_{max}$: 206, 273, 305 nm; IR(KBr) ν 3216, 3158, 3087, 3033, 2923, 2831, 1598, 1562, 1533, 1475, 1340, 1307, 1228, 1166, 1107, 1018, 910, 862, 823, 692, 586, 505 cm$^{-1}$; $^1$H NMR (CDCl$_3$) δ 11.24 (bs, 1H), 9.67 (bs, 1H), 8.07–8.06 (d, 1H), 7.61–7.57 (dt, 1H), 6.99–6.96 (d, 1H), 5.60 (s, 1H), 3.85–3.79 (q, 2H), 2.35–2.31 (t, 2H), 2.02–2.00 (d, 4H), 1.67–1.57 (m, 4H); $^{13}$C NMR (CDCl$_3$) δ 178.5, 151.6, 143.9, 138.4, 134.4, 125.0, 124.0, 113.2, 44.0, 36.8, 27.7, 25.4, 22.8, 22.3;

N-[2-(5-Bromopyridinyl)]-N'-[2-(Pyridinyl)]thiourea (HI-142) (Trovirdine) yield 55%; mp: 152–154° C.; UV(MeOH) $\lambda_{max}$: 208, 273, 306, 485 nm; IR(KBr) ν 3224, 3156, 3085, 3039, 2931, 1583, 1558, 1531, 1465, 1432, 1361, 1319, 1263, 1228, 1166, 1135, 1095, 1012, 885, 825, 756, 700, 661, 567, 511 cm$^{-1}$; $^1$H NMR (CDCl$_3$) δ 11.55 (bs, 1H), 9.56 (bs, 1H), 8.61–8.60 (d, 1H), 8.08–8.07 (d, 1H), 7.71–7.62 (m, 2H), 7.29–7.18 (m, 2H), 6.89–7.86 (d, 1H), 4.24–4.17 (q, 2H), 3.25–3.21 (t, 2H); $^{13}$C NMR (CDCl$_3$) δ 178.7, 158.6, 151.6, 148.9, 146.2, 140.9, 136.6, 123.6, 121.6, 113.5, 112.6, 44.9, 36.6.

Example 2

Modeling of Designed Thiourea Inhibitors to the NNI Binding Pocket

A computer simulation of the binding of the designed thiourea inhibitors to the NNI binding pocket was accomplished using a molecular docking procedure as described in Vig et al., 1998, Bioorg. Med. Chem. 6:1789; Mao, et. al. 1998, Bioorg. Med. Chem. Lett. 8:2213. Once the final energetically favored docked position of the inhibitor in the NNI binding pocket was identified, the inhibitor was assigned an interaction score, from which the inhibition constant ($K_i$) was estimated. The docking results indicated that the cyclohexenyl group of the designed compounds N-[2-(1-cyclohexenyl)ethyl]-N'-[2-(5-bromopyridyl)]-thiourea (HI-346), and N-[2-(1-cyclohexenyl)ethyl]-N'-[2-(5-chloropyridyl)]-thiourea (HI-445) is situated in the Wing 2 region of the NNI binding pocket, providing contact with RT residues including Y181.

The cyclohexenyl group is slightly better than the pyridyl group of trovirdine relative to its hydrophobic interactions with the RT residues. According to our modeling studies, the cyclohexenyl group of the designed lead compound N-[2-(1-cyclohexenyl)ethyl]-N'-[2-(5-bromopyridyl)]-thiourea (HI-346) makes 94 hydrophobic contacts with the surrounding RT residues, including P95, Y181, L100, V179, and Y188, and translates into a 3.0 log unit gain in the final interaction score.

Data are shown below in Table 1. Modeling data are shown in Table 1, which indicates the interaction scores and calculated $K_i$ values of cyclohexenyl containing thiourea compounds. In the table, the hydrophobic score (a) is the Jain' score function; the Polar score (b) indicates hydrogen bonding; the solvent effect term (c); and entropic term (d). N.D. indicates not determined.

TABLE 1

| Compound | X | Hydrophobic Score[a] | Polar Score[b] | Solvent c | Entropic d | $K_i$ (μM) |
|---|---|---|---|---|---|---|
| HI-346 | Br | 10.2 | 1.7 | −1.8 | −3.3 | 0.16 |
| HI-445 | Cl | 9.7 | 1.7 | −1.9 | −3.2 | 0.50 |
| HI-347 | CF$_3$ | 8.8 | 0.2 | −1.6 | −3.3 | 63 |
| Trovirdine | | 10.2 | 0.5 | −1.2 | −3.3 | 0.63 |

The pyridyl group of the reference compound trovirdine bound to the same region of RT would make 81 contacts with surrounding residues, resulting in a 2.7 log unit gain in the final interaction score. The alicyclic cyclohexenyl group contains more ring hydrogens than the heterocyclic pyridyl ring and therefore has more hydrogen atom-mediated contacts and fewer carbon atom-mediated contacts with RT residues than the latter.

Our composite binding pocket also indicated a region in Wing 1 which would be compatible with polar atoms; this region corresponds to the predicted location of the bound halogen atoms of HI-346 and HI-445. The bromine atom of HI-346 makes 21 contacts with 7 RT residues including H235, L234, and V106, because of its large van der Waal radius. The estimated values for the hydrophobic score function in log units were 10.2 for HI-346, and 9.7 for HI-445, whereas the estimated values for the polar score function in log units were 1.7 for HI-346 as well as HI-445. The estimated Ki values were 0.16 μM for HI-346 and 0.50 μM for HI-445.

Example 3

Antiviral Activity of Substituted Thiourea Compounds

Purified RT Assays for Anti-HIV Activity

The synthesized compounds were tested for RT inhibitory activity (IC$_{50}$[rRT]) against purified recombinant HIV RT using the cell-free Quan-T-RT system (Amersham, Arlington Heights, Ill.), which utilizes the scintillation proximity assay principle as decribed in Bosworth, et al., 1989, Nature 341:167–168. In the assay, a DNA/RNA template is bound to SPA beads via a biotin/strepavidin linkage. The primer DNA is a 16-mer oligo(T) which has been annealed to a poly(A) template. The primer/template is bound to a strepavidin-coated SPA bead.

$^3$H-TTP is incorporated into the primer by reverse transcription. In brief, $^3$H-TTP, at a final concentration of 0.5 μCi/sample, was diluted in RT assay buffer (49.5 mM Tris-Cl, pH 8.0, 80 mM KCl, 10 Mm MgCl$_2$, 10 mM DTT, 2.5 mM EGTA, 0.05% Nonidet-P-40), and added to annealed DNA/RNA bound to SPA beads. The compound being tested was added to the reaction mixture at 0.001

$\mu$M–100 $\mu$M concentrations. Addition of 10 mU of recombinant HIV RT and incubation at 37° C. for 1 hour resulted in the extension of the primer by incorporation of $^3$H-TTP. The reaction was stopped by addition of 0.2 ml of 120 mM EDTA. The samples were counted in an open window using a Beckman LS 7600 instrument and $IC_{50}$ values were calculated by comparing the measurements to untreated samples.

In addition, the anti-HIV activity of the compounds was measured by determining their ability to inhibit the replication of the HIV-1 strains HTLVIIIB, RT-MDR, A17, and A17 variant in peripheral blood mononuclear cells (PBMC) from healthy volunteer donors, using the method described in Uckun et.al., 1998, *Antimicrobial Agents and Chemotherapy* 42:383.

Normal human peripheral blood mononuclear cells (PBMNC) from HIV-negative donors were cultured 72 hours in RPMI 1640 supplemented with 20% (v/v) heat-inactivated fetal bovine serum (FBS), 3% interleukin-2,2 mM L-glutairine, 25 mM HEPES, 2 $\mu$L, NAHCO, 50 mg/mL gentamicin, and 4 $\mu$g/mL phytohemagglutinin prior to exposure to HIV-1 or other HIV strain at a multiplicity of infection (MOI) of 0.1 during a one-hour adsorption period at 37° C. in a humidified 5% $CO_2$ atmosphere. Subsequently, cells were cultured in 96-well microplates (100 $\mu$L/well; 2×10$^6$ cells/mL, triplicate wells) in the presence of various inhibitor concentrations. Aliquots of culture supernatants were removed from the wells on the 7$^{th}$ day after infection for p24 antigen p24 enzyme immunoassays (EIA), as previously described in Erice et al., 1993, *Antimicrob. Ag. Chemotherapy* 37:385–838. The applied p24 EIA was the unmodified kinetic assay commercially available from Coulter Corporation/Immunotech, Inc. (Westbrook, Me.). Percent inhibition of viral replication was calculated by comparing the p24 values from the test substance-treated infected cells with p24 values from untreated infected cells (i.e, virus controls).

A microculture tetrazolium Assay (MTA), using 2,3-bis (2-methoxy-4-nitro-5-sulfophenyl)-5-[(phenylarnino)-carbonyl]-2H-tetrazolium hydroxide (XTT), was performed to evaluate the cytotoxicity of the compounds, using the methods described, for example, in Uckun et. al., 1998, *Antimicrobial Agents and Chemotherapy* 42:383; and Mao et. al., 1998, *Bioorg. Med. Chem. Lett.* 8:2213. Data are reported as $CC_{50}$ ($\mu$M).

Activity Against Drug-Resistant HIV Strains

The activity of the CHET compounds, HI-445 and HI-346, was tested against drug sensitive strains (HTLV IIIB), NNI-resistant strains (A17 and A17 variant), as well as multidrug resistant HIV-1 strains (RT-MDR), using the method described in Ucken et al. 1998, *Antimicrobial Agents and Chemotherapy* 42:383. RT-MDR was obtained through the AIDS Research and Reference Reagent Program, from Dr. Bendan Larder, and is described in Larder et al., 1993, *Nature*, 365, 451–453.

Data are presented in Table 2 as the $IC_{50}$ values for inhibition of HIV p24 antigen production in PBMC (concentration at which the compound inhibits p24 production by 50%). Both CHET compounds, HI-346 and HI-445, were more effective than trovirdine, and more effective than as the control NNI compounds nevirapine and delavirdine, in inhibiting recombinant RT. Furthermore, both CHET compounds were slightly more effective than trovirdine, and the control anti-HIV compounds nevirapine, delavirdine, MKC-442, and AZT, in inhibiting the replication of the NNI-sensitive/AZT-sensitive HIV-1 strain HTLVIIIB (see Table 2).

TABLE 2

$$R_2 \diagdown \diagdown \underset{S}{\overset{H}{N}} \diagdown \underset{}{\overset{H}{N}} \diagdown \text{pyridyl-X}$$

| Compound | $R_2$ | X | $IC_{50}$ rRT ($\mu$M) | $IC_{50}$ HTLV$_{III}$B ($\mu$M) | $IC_{50}$ RT-MDR ($\mu$M) | $IC_{50}$ A17 ($\mu$M) | $IC_{50}$ A17 variant ($\mu$M) | $CC_{50}$ MTA ($\mu$M) |
|---|---|---|---|---|---|---|---|---|
| Trovirdine | Pyridyl | Br | 0.8 | 0.007 | 0.020 | 0.500 | >100 | >100 |
| HI-346 | Cyclohexenyl | Br | 0.4 | 0.003 | 0.001 | ND | 18.7 | >100 |
| HI-445 | Cyclohexenyl | Cl | 0.5 | 0.003 | 0.001 | 0.068 | 30.0 | >100 |
| HI-347 | Cyclohexenyl | CF$_3$ | 4.0 | 0.079 | 0.038 | 0.300 | >100 | >100 |
| HI-504 | Adamentyl* | Br | >100 | ND | ND | ND | ND | ND |
| HI-444 | Myrtanyl* | Br | >100 | ND | ND | ND | ND | ND |
| Nevirapine | — | — | 23 | 0.034 | 5.0 | >100 | >100 | 10.5 |
| Delavirdine | — | — | 1.5 | 0.009 | 0.4 | 50.0 | >100 | 3.6 |
| MKC-442 | — | — | 0.8 | 0.004 | 0.3 | ND | ND | >100 |
| AZT | — | — | — | 0.004 | 0.2 | 0.006 | 0.004 | >100 |

*methylene group instead of ethyl linker
ND = not done

Unlike CHET compounds HI-346 and HI-445, the control cyclohexenyl containing thiourea compound N-[2-(1-cyclohexenyl)ethyl]-N'-[2-(5-trifluoromethylpyridyl)]-thiourea (HI-347), for which we had estimated a relatively poor $K_i$ value of 63 $\mu$M, was significanly less potent than trovirdine in both RT inhibition assays and HIV replication assays. Replacement of the pyridyl ring of trovirdine with the alicyclic substituents adamantyl or cis-myrtanyl (instead of cyclohexenyl) ($R_2$) resulted in complete loss of RT inhibitory function (Table 2). Thus, the cyclohexenyl moiety ($R_2$) as well as the substitution moiety (x) play critical roles in the anti-HIV activity of HI-346 and HI-445.

Notably, both HI-346 and HI-445 were 3-times more effective against the multidrug resistant HIV-1 strain RT-MDR (V106A mutation and additional mutations involving the RT residues 74V, 41L, and 215Y) than they were against HTLVIIIB. The activity of the lead compound HI-346 against RT-MDR was substantially more potent than the activities of other anti-HIV agents tested. The ranking order of potency against RT-MDR was: HI-346 ($IC_{50}$=1 nM)=HI-445 ($IC_{50}$=1 nM)>trovirdine ($IC_{50}$=20 nM)>AZT ($IC_{50}$=200 nM)>MKC-442 ($IC_{50}$=300 nM)>delavirdine ($IC_{50}$=400 nM)>nevirapine ($IC_{50}$=5000 nM). HI-346 and HI-445 were 20-times more potent than trovirdine, 200-times more potent than AZT, 300-times more potent than MKC-442, 400-times more potent than delavirdine, and 5000-times more potent than nevirapine against the multidrug resistant RT-MDR strain.

HI-445 was also tested against the RTY181C mutant A17 strain and found to be >7-fold more effective than trovirdine, and >1,400-fold more effective than nevirapine or delavirdine. Similarly, both HI-346 and HI-445 were more effective than trovirdine, nevirapine, and delavirdine against the trovirdine-resistant A17 variant with both Y181C and K103N mutations in RT. Neither compound exhibited significant toxicity at effective concentrations. These findings establish the cyclohexenyl-containing thiourea compounds, and particularly, HI-346 and HI-445, as potent NNI useful against sensitive as well as multidrug-resistant strains of HIV-1.

All publications, patents, and patent documents described herein are incorporated by reference as if fully set forth. The invention described herein may be modified to include alternative embodiments. All such obvious alternatives are within the spirit and scope of the invention, as claimed below.

We claim:

1. A method for inhibiting HIV reverse transriptase comprising:

administering to a subject, having a strn of HIV having a mutated HIV reverse transcriptase comprising one or more of the following amino acid substitutions: K103N, V106A or Y181C, an effective therapeutic amount of at least one compound selected from;

N-[2-(1-cyclohexenyl)ethyl]-N'-[2-(5-bromopyridyl)]-thiourea;

N-[2–1-cyclohexenyl)ethyl]-N'-[2-(5-chloropyridyl)]-thiourea; and a pharmaceutically acceptable addition salt thereof;

wherein said compound inhibits said strain of HIV reverse transcriptase.

2. A method for inhibiting HIV reverse transcriptase comprising:

administering to a subject, having one or more non-nucleoside inhibitor-resistant strain of HIV, an effective therapeutic amount of at least one non-nucleoside inhibitor compound selected from;

N-[2-(1-cyclohexenyl)ethyl]-N'-[2-(5-broinopyridyl)]-thiourea;

N-[2-(1-cyclohexenyl)ethyl]-N'-[2-(5-chloropyridyl)]-thiourea; and a pharmaceutically acceptable addition salt thereof.

* * * * *